United States Patent [19]

Baker

[11] Patent Number: 5,190,760
[45] Date of Patent: Mar. 2, 1993

[54] SOLID PHARMACEUTICAL COMPOSITION

[75] Inventor: Rodney C. Baker, Hertsfordshire, England

[73] Assignee: Coopers Animal Health Limited, Hertfordshire, England

[21] Appl. No.: 887,393

[22] Filed: May 21, 1992

Related U.S. Application Data

[63] Continuation of Ser. No. 548,712, Jul. 6, 1990, abandoned.

[30] Foreign Application Priority Data

Jul. 8, 1989 [GB] United Kingdom ............... 8915716

[51] Int. Cl.$^5$ ................................................. A23K 1/18
[52] U.S. Cl. ..................................... 424/438; 424/472; 424/480; 424/482
[58] Field of Search ................ 424/438, 480, 482, 472

[56] References Cited

U.S. PATENT DOCUMENTS

| | | | |
|---|---|---|---|
| 3,773,921 | 11/1973 | Sheth et al. | 424/480 |
| 4,181,708 | 1/1980 | Dannelly | 424/19 |
| 4,612,186 | 9/1986 | Eckenhoff | 424/15 |
| 4,643,893 | 2/1987 | Ascher | 424/16 |
| 4,789,548 | 12/1988 | Tisdale | 424/472 |
| 4,865,849 | 9/1989 | Conte | 424/466 |
| 5,082,669 | 1/1992 | Shirai | 424/482 |

FOREIGN PATENT DOCUMENTS

| | | |
|---|---|---|
| 838506 | 2/1976 | Belgium . |
| 0236002 | 2/1987 | European Pat. Off. . |
| 0238207 | 9/1987 | European Pat. Off. . |
| 1330829 | 9/1973 | United Kingdom . |
| 1499672 | 2/1978 | United Kingdom . |

Primary Examiner—Thurman K. Page
Assistant Examiner—D. Gabrielle Phelan
Attorney, Agent, or Firm—Nixon & Vanderhye

[57] ABSTRACT

A solid pharmaceutical composition for release of a biologically active substance into a desired aqueous environment, containing a core and an outer layer, said core comprising between 17 and 93% by weight of the biologically active substance, between 0.01 and 7% by weight of a water swellable polymer material and between 0 and 83% of one or more accessory ingredients, relative to the total weight of the core; and the outer layer comprising between 25 and 75% by weight of the biologically active substance, between 25 and 75% by weight of a material for enabling rapid dispersion of the outer layer into the aqueous environment and 0 to 50% by weight of one or more accessory ingredients, relative to the total weight of the outer layer. The composition is preferably formulated as a bolus for veterinary use.

14 Claims, No Drawings

SOLID PHARMACEUTICAL COMPOSITION

This is a continuation of application Ser. No. 07/548,712, filed Jul. 6, 1990, now abandoned.

The present invention relates to pharmaceutical compositions and unit dose forms for the administration of biologically active substances to animals, particularly ruminants.

European Patent Application No. 236002 discloses pharmaceutical compositions for release of drug over a prolonged period by incorporating a water swellable polymer, such as a cellulose ether, in the composition. The water swellable polymer is preferably present at a weight concentration of between 0.1 and 1.0%. To achieve a particular release profile, e.g. an immediate release followed immediately afterwards, or after an interval, by a slower prolonged release, a mixture of two or more different formulations is described, for example two or more forms of granules each containing a different percentage of polymer.

It has now been found that an initial dose of drug followed by prolonged release of the drug may be obtained by forming a core having a composition as described in European Patent Application No. 236002 and coating this with an outer layer comprising drug and a high percentage of water soluble or water swellable polymer which may be the same or different to the polymer contained in the core.

Accordingly, the present invention provides a solid pharmaceutical composition for release of a biologically active substance into a desired aqueous environment, containing a core and an outer layer, said core comprising between 17 and 93% by weight of the biologically active substance, between 0.01 and 7% by weight of a water swellable polymer material and between 0 and 83% of one or more accessory ingredients, relative to the total weight of the core; and the outer layer comprising between 25 and 75% by weight of the biologically active substance, between 25 and 75% by weight of a material for enabling rapid dispersion of the outer layer into the aqueous environment and 0 to 50% by weight of one or more accessory ingredient, relative to the total weight of the outer layer.

A pharmaceutical composition according to the present invention may be formulated for use in human or veterinary medicine but is preferably used in veterinary medicine. Such formulations may be presented, for example, in unit dose form.

A unit dose form according to the present invention may be for example a pharmaceutical unit dose for oral administration to a human or animal such as a bolus, tablet, cachet or lozenge. In the present invention, dosage forms adapted for veterinary use are preferred.

Especially preferred dosage forms for administration to ruminant animals (e.g. cattle and sheep) are boluses wherein the ingredients are present in the form of compressed powders or granules. To inhibit regurgitation of an intra-rumenal bolus, the bolus should be provided with retention means, for example, a discrete weight such as described in European Patent Specification No: EP 0 164 927 A2 or a densification material mixed with the composition, i.e. as the or one of the said accessory ingredients. Preferably a bolus of the present invention is retained in the rumen by incorporation of iron powder as a densification material. Other suitable densification materials include iron filings, other dense metals such as tungsten and dense inorganic compounds, such as for example barium sulphate, calcium sulphate and calcium phosphate.

Biologically active substance suitable for incorporation in a pharmaceutical composition according to the present invention include pharmacologically active agents such as anti-infectives, e.g. antibacterials and anthelmintics; animal growth promoters; and animal nutrients. Other biologically active substances which may be administered to animals include insecticides and larvicides. In general the biologically active substance may be any of those described in European Patent Specification No. 164 927.

Preferred pharmacological agents for veterinary use include anti-infective agents such as anthelmintics and antibacterials.

Preferred antibacterials include sulphonamides and salts thereof (e.g. sulfanilamide, sulfadiazine, sulfamethoxazole, sulfapyridine, sulfathiazole, sulfamerazine, sulfamethazine, sulfisoxazole, sulformethoxine, 2-(p-aminobenzene)-sulfonamide-3-methoxypyrazine (Kelfizina), sulfonyldianiline, mafenide, 5-sulfanilamido-2,4-dimethylpyrimidine, 4-(N'-acetylsulfanilamide)-5,6-dimethoxypyrimidine, 3-sulfanilamido-4,5-dimethylisoxazole, 4-sulfanilamido-5-methoxy-6-decyloxypyrimidine-sulfamono-methoxine, 4-p-(8-hydroxyquinolinyl-4-azo)phenylsulfanilamido-5,6-dimethoxypyrimidine, sulfadimethoxine, sulfadimidine, sulfamethoxazole, sulfamoxole, sulfadoxine, sulfaguanidine, sulfathiodimethoxine, sulfaquinoxaline, and p-(2-methyl-8-hydroxyquinolinyl-5-azo)-phenylsulfanilamido-5,6-dimethoxyprimidine); and 2,4-diaminopyrimidines and salts thereof (e.g. 2,4-diamino-6-ethyl-5-p-chlorophenylpyrimidine (Pyrimethamine), 2,4-diamino-5-(3',4',5'-trimethoxybenzyl)pyrimidine (Trimethoprim), 2,4-diamino-5-(3',4'-dimethoxybenzyl)-pyrimidine (Diaveridine), 2,4-diamino-5-(2'-isopropyl-4'-chlorophenoxy) pyrimidine, 2,4-diamino-5-methyl-6-sec-butyl-pyrido(2,3-d)pyrimidine, 2,4-diamino-5-methyl-6-benzylpyrido (2,3-d)-pyrimidine, 2,4-diamino-6-benzyl-pyrido(2,3-d)pyrimidine, 2,4-diamino-5,6-trimethylenequinazoline, 2,4-diamino-5,6-tetramethylenequinazoline, 2,4-diamino-5-(4'-dimethylamino-3',5'-dimethoxybenzyl)pyrimidine, 2,4-diamino-5-(2',4',5'-trimethoxybenzyl)pyrimidine, 2,4-diamino-5-(2'-ethyl-4',5'-dimethoxybenzyl)pyrimidine, and 2,4-diamino 5-(2'-methyl-4',5'-dimethoxy-benzyl) pyrimidine (Ormetoprim), as well as the 2,4-diaminopyrimidine derivatives disclosed in European Patent No. 51879). A particularly preferred 2,4-diaminopyrimidine for use in pharmaceutical compositions according to the present invention is 2,4-diamino-5-(8-dimethylamino-7-methyl-5-quinolylmethyl)pyrimidine (Baquiloprim) or a salt thereof. A particularly preferred sulphonamide is sulphadimidine or a salt thereof.

Preferred anthelmintics include levamisole, tetramisole, oxfendazole, mebendazole, fenbendazole, thiabendazole, albendaxole and ivermectin.

The material for enabling rapid dispersion of the outer layer into the aqueous environment is suitably a film-forming material that is soluble or swellable in the aqueous environment, for example a water swellable or water soluble polymer, or a material that is flowable, e.g. liquid, at the temperature of the aqueous environment but is non-flowable at the normal storage temperature of the composition (the normal storage temperature of the composition is suitably less than 30° C. and preferably less than 20° C.).

Water-soluble polymers which may be utilised in the outer layer of the composition of the present invention are water-soluble film-forming substances such as polyvinyl alcohol, polyvinylpyrrolidone, gelatin and polyethylene oxide.

Water-swellable polymers which may be utilised in the core and/or outer layer of the composition of the present invention include cellulose ethers, generally those having a number average molecular weight in the range 10,000 to 250,000, such as cellulose ethers, for example methylcellulose and hydroxypropylmethylcellulose (HPMC) such as are sold under the trade names "Methocel" and "Opadry" ("Opadry" is primarily hydroxypropylmethylcellulose to which has been added accessory ingredients to optimise its physical properties). Preferably the water swellable polymer is hydroxypropylmethylcellulose, most preferably "Methocel" E5, E50-LV, K15M, K100M and E4M and "Opadry" OY-S-7251.

Flowable materials which may be utilised in the outer layer of the composition of the present invention include surfactants, for example "Pluronics", waxes, for example paraffin waxes, coating butter, milk solids and glycerides.

The water swellable polymer is preferably present in the core of the composition at a % weight concentration of between 0.01 to 5.0%, e.g. 0.1 to 4.0%, especially 0.5 to 2.5%, for example about 1%.

Preferably the polymer in the outer layer is a water swellable polymer. The water swellable polymer is preferably present in the outer layer of the composition at a % weight concentration of between 40% and 60% by weights and preferably about 50%.

Accessory ingredients which may be incorporated in a pharmaceutical composition according to the present invention are well known to those skilled in the art of human and veterinary pharmacy. Thus, accessory ingredients may include densification agents as described above; dense, water insoluble fillers (bulking agents) such as dibasic calcium phosphate, barium sulphate, or other fillers as described in U.S. Pat. No. 3,773,921; binders, such as polyvinylpyrrolidone, gelatin, casein, acacia, tragacanth, agar and pectin; and lubricants such as magnesium stearate, sodium stearate, calcium stearate, stearic acid, talc or silica. If desired the formulations may also contain pigments such as red or yellow iron oxide.

Preferred compositions according to the present invention are those comprising a biologically active substance, water swellable polymer material and optionally, one or more accessory ingredients in the core, characterised in that the water swellable polymer material in the core constitutes no more than 2% by weight of said composition, for example between 0.1 and 1% by weight of polymer.

It will be appreciated that the type and amounts of accessory ingredients may be varied depending on the precise formulation required.

Densification agents will generally be present at concentrations of from 5 to 75% by weight of the total composition, preferably 15 to 50%. Densification agents will normally be present in the core of the composition.

Fillers will generally comprise 0 to 95% of the total composition. Binding agents are preferably present in an amount ranging from 1 to 10% and lubricants in the range 0.1 to 2%. Colouring agents, e.g. pigments or dyes, may be distributed throughout the outer layer, and optionally the core, of the composition but will normally form a surface film of pigmented material around the composition, for example a film of a hydroxypropylmethyl cellulose containing a colouring agent, e.g. "Opadry" OY-4980.

Pharmaceutical dosage forms according to the present invention may be prepared by techniques known to those skilled in the art of human and veterinary pharmacy. Thus, for example the core may be prepared by direct compression of the admixed ingredients. Alternatively, the ingredients may first be granulated and the granules compressed. When the core is prepared by granulation it may be convenient to add a lubricant e.g. magesium stearate after the granulation step. As will be understood by those skilled in the art, the degree of compression will affect the hardness of the dosage form. It is preferred that, when measured by the method described hereinafter, the hardness of dosage forms according to the present invention lies in the range 100 to 18,000 Newtons, preferably 1200 to 1800N for a 30 g bolus and 30 to 900N for a 15 g bolus. It will be appreciated however that the optimum hardness and the degree of compression required for a given dosage form can readily be determined by routine tests.

The outer layer may be prepared by dissolving and/or suspending the outer layer components, including the biologically active substance, in an appropriate liquid medium e.g. water. The resulting solution or dispersion may then be applied to the core by coating methods known in the art. Such methods include spray coating, for example in a pan coater.

The hardness of the unit dose forms prepared in accordance with the present invention is measured using a T30K Tensometer (J. J. Lloyd), modified so as to locate the dosage form in a 3-point pivot. The dosage form e.g. a bolus is supported on two lower pins which move in an upward direction until the dosage form meets an upper pin located midway between the two lower pins. Pressure is applied until the dosage form breaks and the force required to reach this point is recorded.

It will be appreciated that whilst the amounts of polymer present in the core and the amount of dispersing material in the outer layer are critical factors in determining the release rate of the active ingredient, the precise duration and pattern of release will be affected to some extent by other factors such as the nature of the active ingredient, the particle size of the active ingredient, the degree of compression used in manufacturing the dosage form and its overall size. It may be convenient for the core to have one particle size of active ingredient whilst the outer layer may have a different particle size, for example a more coarse size, of active ingredient to optimise the release characteristics of the composition. In general a unit dosage form according to the present invention may provide release of the active ingredient for up to 10 days. Thus, the outer layer of the composition may provide an initial therapeutic dose of active ingredient within two hours of administration and the core may provide continuous release of the active ingredient over a period of 5 to 240 hours e.g. 10 to 168 hours from the time of administration.

In one aspect the present invention provides a solid pharmaceutical composition for release of a biologically active substance into a desired aqueous environment, containing a core and an outer layer, said core comprising between 17 and 93% by weight of the biologically active substance, between 0.01 and 2% by weight of a water swellable polymer material and between 0 and 83% of one or more accessory ingredients, relative to the total weight of the core; and the outer layer comprising between 25 and 75% by weight of the biologically active substance, between 25 and 75% by weight of a water swellable or water soluble polymer and 0 to 10% by weight of one or more accessory ingredients, relative to the total weight of the outer layer.

In a preferred embodiment the present invention provides a veterinary bolus for oral administration to the rumen of an animal said bolus comprising one or more active ingredients, preferably an antibacterial agent such as 2,4-diamino-5-(8-dimethylamino-7-methyl-5-quinolylmethyl)pyrimidine or a salt thereof and/or a sulphonamide preferably sulphadimidine, or a salt thereof, together with a water swellable polymer, preferably hydroxypropylmethylcellulose, characterised in that it contains a core comprising from 1 to 5% of the pyrimidine, preferably about 3% of the pyrimidine, and from 16 to 80% of the sulphonamide, preferably about 49 to 52% e.g. 51 to 52% of sulphadimidine, 0.1 to 2%, and preferably 0.5 to 1.5%, of the water swellable polymer, preferably hydroxypropylmethylcellulose and optionally a total of from 5 to 83%, suitably from 20 to 60% and preferably 40 to 50%, of accessory ingredients including binders, lubricants, densification agents for example iron powder, and pigments (percentages of core ingredients being by weight, relative to the total weight of the core) and an outer layer comprising from 10 to 20%, preferably about 13 to 15% e.g. about 14%, of the pyrimidine, 30% to 40%, preferably 34 to 36% e.g. about 35% of the sulphonamide, 20 to 60%, preferably 30 to 40% of a water swellable polymer, preferably hydroxypropylmethylcellulose, and 0 to 30%, preferably 10 to 20% of accessory ingredients including plasticisers and pigments (the percentages of outer layer ingredients being by weight relative to the total weight of the outer layer). The bolus is optionally coated with a water swellable polymer containing pigment which preferably comprises 0.5 to 5% by weight of the total weight of the composition. This pigment coating is in turn optionally coated with a protective film preventing pigment leaching out of the composition onto the operator administering the composition. In this embodiment the bolus typically provides to the animal from 1 to 24 mg/kg of the pyrimidine, preferably approximately 8 to 16 mg/kg; and from 9 to 216 mg/kg of sulphadimidine, preferably approximately 72 to 144 mg/kg. The unit dose form conveniently has a total weight of from 5 to 50 g. The length of the bolus is conveniently in the range 30 to 70 mm preferably 50 to 55 mm, and its thickness is within the range 10 to 30 mm, e.g. 10 to 14 mm for a 15 g bolus and 18 to 23 mm for a 30 g bolus.

The present invention also provides a method of treating a bacterial or helminthic infection which comprises the administration of a pharmaceutical composition as hereinbefore defined.

In a preferred embodiment the distribution of the total amount of pyrimidine in the bolus between the core and the outer layer is in the ratio 5:1 to 1:5, preferably 2:1 to 1:2, most preferably 1:1. The total amount of sulphonamide is distributed between the core and the coat in the ratio 20:1 to 1:15, preferably 10:1 to 1:5 most preferably 5:1 to 6:1.

In a further aspect, the present invention provides a pharmaceutical composition, as hereinbefore defined, for use in use in the treatment or control of bacterial or helminth infections in animals.

The present invention will now be illustrated by way of the following non-limiting examples. Baquiloprim is 2,4-diamino-5-(8-dimethylamino-7-methyl-5-quinolylmethyl)pyrimidine. SDD is sulphadimidine.

Example 1

|  | g/kg in Bolus | g/kg in core | g/kg in coat 1 | g/kg in coat 2 | In One Bolus (g) |
|---|---|---|---|---|---|
| Active Constituents |  |  |  |  |  |
| Baquiloprim | 53.3 | 33.3 | 140.3 | — | 1.60 |
| Sulphadimidine BP/Ph Eur | 79.7 | 516.3 | 350.9 | — | 14.39 |
| Other Constituents |  |  |  |  |  |
| Reduced Iron Powder | 226.7 | 283.4 | — | — | 6.80 |
| Calcium Hydrogen Phosphate Ph Eur | 80.0 | 100.0 | — | — | 2.40 |
| Hydroxypropyl Methylcellulose 2208 USP | 8.0 | 10.0 | — | — | 0.24 |
| Povidone BP (K30) | 40.0 | 50.0 | — | — | 1.20 |
| Tartrazine | 1.6 | 2.0 | — | — | 0.05 |
| Magnesium Stearate BP | 4.0 | 5.0 | — | — | 0.12 |
| Opadry OY-S-7251 | 96.7 | — | 508.8 | — | 2.90 |
| Opadry OY-4980 (Red) | 10.0 | — | — | 1000.0 | 0.30 |
|  | 1000.0 | 1000.0 | 1000.0 | 1000.0 | 30.00 |

MANUFACTURE OF DOSAGE FORM

The active constituents to be incorporated in the core, the Iron Powder, Calcium Hydrogen Phosphate and Hydroxypropyl Methylcellulose were intimately mixed as dry powders. Povidone K30 was dissolved in an aqueous alcoholic mixture; and to this was added an aqueous solution of the Tartrazine. This solution was used to granulate the mixed powders. After drying, the granules were sieved and the Magnesium Stearate blended in. The granules were compressed on a reciprocating tabletting machine to form Boluses of nominal weight 24 g.

The remainder of the active constituents were dispersed in an aqueous solution of the Opadry OY-S-7251 (Coat 1). This dispersion was sprayed onto the Boluses in a Huttlin "Butterfly" coating machine until the Bolus weight was 29.7 g. Finally the Opadry OY-4980 was dispersed in water (Coat 2) and sprayed onto the Bolus to impart a red colour and increase the weight to 30 g.

Example 2

Granules prepared as in Example 1 were compressed to form boluses of nominal weight 12 g. These were sprayed with Coat 1, prepared as in Example 1, to give boluses of weight 14.85 g and subsequently sprayed with Coat 2, also prepared as in Example 1, to give a final weight of 15 g per bolus.

SERUM PROFILES FOLLOWING ORAL ADMINISTRATION TO CATTLE

Example 3

(30 g Bolus)

Four healthy cross-bred beef-type cattle (nos 1–4) each received by oral administration a single 30 g bolus formulated according to Example 1, shown by assay to contain in the core 3.22% w/w baquiloprim and 50.0% w/w SDD, and in the coating 13.59 w/w baquiloprim and 36.23% w/w SDD. Blood samples were taken from each animal before dosing and at 1, 3, 5, 8, 12, 24, 31, 48, 55, 72, 79, 96, 103 and 120 hours after administration. The concentrations of baquiloprim and SDD in the serum were determined by bio-assay and the Bratton-Marshall colorimetric method respectively. The results are presented in Table 1 below.

TABLE 1

Serum concentrations (mg/L) of Baquiloprim (B) and Sulphadimidine (S) in cattle dosed with 30 g bolus

| Hours | Animal (bodyweight) | | | | | | | |
|---|---|---|---|---|---|---|---|---|
| | 1 (160 kg) | | 2 (165 kg) | | 3 (175 kg) | | 4 (170 kg) | |
| | B | S | B | S | B | S | B | S |
| 1 | 0 | 3 | 0 | 0 | 0.08 | 7 | 0 | 3 |
| 3 | 0.11 | 8 | 0.08 | 7 | 0.15 | 15 | 0.14 | 13 |
| 5 | 0.16 | 13 | 0.15 | 13 | 0.21 | 21 | 0.20 | 20 |
| 8 | 0.21 | 16 | 0.20 | 14 | 0.27 | 25 | 0.28 | 26 |
| 12 | 0.25 | 18 | 0.23 | 18 | 0.38 | 28 | 0.37 | 30 |
| 24 | 0.43 | 25 | 0.42 | 20 | 0.52 | 30 | 0.62 | 32 |
| 31 | 0.47 | 25 | 0.41 | 24 | 0.49 | 29 | 0.62 | 32 |
| 48 | 0.53 | 23 | 0.49 | 21 | 0.52 | 23 | 0.55 | 25 |
| 55 | 0.40 | 23 | 0.29 | 18 | 0.43 | 21 | 0.45 | 22 |
| 72 | 0.30 | 17 | 0.23 | 15 | 0.31 | 18 | 0.31 | 16 |
| 79 | 0.27 | 15 | 0.19 | 14 | 0.27 | 16 | 0.31 | 14 |
| 96 | 0.19 | 12 | 0.15 | 9 | 0.23 | 12 | 0.23 | 20 |
| 103 | 0.18 | 9 | 0.13 | 8 | 0.21 | 12 | 0.20 | 14 |
| 120 | 0.14 | 2 | 0.10 | 8 | 0.20 | 10 | 0.15 | 5 |

Baquiloprim and Sulphadimidine were not detected in the predosing samples (ie below 0.04 mg/L and 1 mg/L respectively).

Example 4

(15 g Bolus)

Four healthy Friesian-cross calves of mixed sex (nos 5–8) each received by oral administration a single 15 g bolus formulated according to Example 2 above and shown by assay to contain in the core 3.3% w/w baquiloprim and 49.7% w/w SDD and in the coat 13.20% w/w baquiloprim and 36.0% w/w SDD. Blood samples were taken from each animal before dosing and at 1, 3, 7, 12, 24, 31, 55, 72, 79, 96, 103 and 120 hours after administration. The concentrations of baquiloprim and SDD in the serum were determined as in Example 3. The results are presented in Table 2 below.

TABLE 2

Serum concentrations (mg/L) of Baquiloprim (B) and Sulphadimidine (S) in cattle dosed with 15 g bolus

| Hours | Animal (bodyweight) | | | | | | | |
|---|---|---|---|---|---|---|---|---|
| | 5 (95 kg) | | 6 (90 kg) | | 7 (85 kg) | | 8 (85 kg) | |
| | B | S | B | S | B | S | B | S |
| 1 | 0 | 2.0 | 0 | 5.0 | 0 | 2.5 | 0 | 1.0 |
| 3 | 0.048 | 7.0 | 0.068 | 12.5 | 0.070 | 8.5 | 0.060 | 8.0 |
| 7 | 0.076 | 14.5 | 0.155 | 20.0 | 0.180 | 18.5 | 0.105 | 17.5 |
| 12 | 0.155 | 19.0 | 0.420 | 22.5 | 0.250 | 23.5 | 0.170 | 23.5 |
| 24 | 0.470 | 24.5 | 0.500 | 29.0 | 0.500 | 30.5 | 0.500 | 30.5 |
| 31 | 0.500 | 23.0 | 0.480 | 29.5 | 0.540 | 28.0 | 0.470 | 29.0 |
| 48 | 0.480 | 19.0 | 0.500 | 22.0 | 0.610 | 21.0 | 0.610 | 40.0 |
| 72 | 0.410 | 14.0 | 0.370 | 14.5 | 0.390 | 10.5 | 0.350 | 7.5 |
| 96 | 0.245 | 1.0 | 0.280 | 6.5 | 0.210 | 1.0 | 0.180 | 0.5 |
| 120 | 0.120 | 0 | 0.160 | 0 | 0.150 | 0 | 0.105 | 0 |

I claim:

1. A solid pharmaceutical composition for release of a biologically active substance into a desired aqueous environment, containing a core and an outer layer coated thereon,
   said core consisting essentially of between 17 and 93% by weight of the biologically active substance, between 0.01 and 7% by weight of a water swellable polymer material and between 0 and 83% of one or more accessory ingredients, relative to the total weight of the core; and
   the outer layer consisting essentially of between 25 and 75% by weight of the biologically active substance, between 25 and 75% by weight of a material for enabling rapid dispersion of the outer layer into the aqueous environment and 0 to 50% by weight of one or more accessory ingredients, relative to the total weight of the outer layer.

2. A pharmaceutical composition according to claim 1, in unit dose form.

3. A pharmaceutical composition according to claim 1 for oral administration.

4. A pharmaceutical composition according to claim 1 for veterinary use.

5. A pharmaceutical composition according to claim 4 adapted for oral administration to the rumen of an animal.

6. A pharmaceutical composition according to claim 5 which is an intra-rumenal bolus provided with a means to inhibit regurgitation.

7. A pharmaceutical composition according to claim 1 wherein the material for enabling rapid dispersion of the outer layer is a water-swellable polymer.

8. A pharmaceutical composition according to claim 1 wherein the core contains between 0.01 and 2.0% by weight of a water swellable polymer.

9. A pharmaceutical composition according to claim 1 wherein the biologically active substance is an antibacterial or anthelmintic agent.

10. A pharmaceutical composition according to claim 9 wherein the antibacterial agent comprises a sulphonamide or a salt thereof and/or a 2,4-diaminopyrimidine or a salt thereof.

11. A pharmaceutical composition according to claim 9 wherein the antibacterial agent comprises 2,4-diamino-5-(8-dimethylamino-7-methyl-5-quinolymethyl)pyrimidine or a salt thereof together with sulphadimidine or a salt thereof.

12. A pharmaceutical composition according to claim 11 wherein the core contains from 1 to 5% of the pyrimidine and from 16 to 80% of the sulphonamide and the coating contains from 10 to 20% of the pyrimidine and 30 to 40% of the sulphonamide.

13. A pharmaceutical composition according to claim 12 which provides a dose of 2,4-diamino-5-(8-dimethylamino-7-methyl-5-quinolylmethyl)pyrimidine in the range 1 to 24 mg/kg and a dose of sulphadimidine in the range 9 to 216 mg/kg.

14. A method of treating a bacterial or helminthic infection which comprises administering to an animal in need thereof, a composition as defined in claim 1.

* * * * *